United States Patent [19]

Büchel et al.

[11] 4,005,083
[45] Jan. 25, 1977

[54] METAL COMPLEXES OF AZOLYL ETHERS
[75] Inventors: Karl Heinz Büchel; Wolfgang Krämer, both of Wuppertal; Helmut Kaspers; Hans Scheinpflug, both of Leverkusen, all of Germany
[73] Assignee: Bayer Aktiengesellschaft, Leverkusen, Germany
[22] Filed: Apr. 30, 1975
[21] Appl. No.: 573,212
[30] Foreign Application Priority Data
May 17, 1974 Germany .......................... 2423987
[52] U.S. Cl. .............................. 424/245; 260/299; 260/308 R; 260/309; 424/269; 424/273
[51] Int. Cl.² ................. A01N 9/22; C07D 249/08; C07D 233/60
[58] Field of Search ............... 260/299, 308 R, 309; 424/245, 273, 269

[56] References Cited
UNITED STATES PATENTS

| | | | |
|---|---|---|---|
| 3,647,810 | 3/1972 | Bayer et al. | 260/299 |
| 3,812,142 | 5/1974 | Meiser et al. | 260/309 |
| 3,898,341 | 8/1975 | Meiser et al. | 424/273 |
| 3,912,752 | 10/1975 | Meiser et al. | 260/308 R |
| 3,914,427 | 10/1975 | Krämer et al. | 424/273 |

Primary Examiner—R. Gallagher
Assistant Examiner—Diana G. Rivers
Attorney, Agent, or Firm—Burgess, Dinklage & Sprung

[57] ABSTRACT

Metal complexes of azolyl ethers of the formula

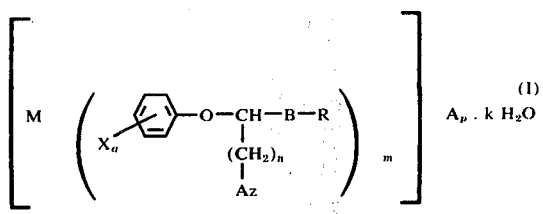

in which
M is a metal,
X is halogen, nitro, nitrile, optionally substituted alkyl, optionally substituted aryl, cycloalkyl, amino, carboxyl, alkoxycarbonyl, alkylcarbonyloxy, alkoxy, alkylthio, halogenoalkoxy, halogenoalkylthio, aryloxy, arylcarbonyloxy, benzoyl, halogenobenzoyl, alkylcarbonylamino, dialkylamino, alkylsulfonyl, alkylsulfonyloxy, arylsulfonyl or arylsulfonyloxy,
Az is an imidazolyl radical, a 1,2,4-triazolyl-(1) radical or a 1,2,4-triazolyl-(4) radical,
B is CO or CH(OH),
R is alkyl or optionally substituted aryl,
A is an anion of an inorganic acid,
$a$ is an integer from 0 to 5,
$n$ is 0 or 1,
$m$ is an integer from 1 to 4,
$p$ is an integer from 1 to 6, and
$k$ is an integer from 0 to 12, which possess fungicidal, bactericidal and plant growth-regulating properties.

12 Claims, No Drawings

METAL COMPLEXES OF AZOLYL ETHERS

The present invention relates to and has for its objects the provision of particular new metal complexes of azolyl ethers which possess fungicidal, bactericidal and plant growth-regulating properties, active compositions in the form of mixtures of such compounds with solid and liquid dispersible carrier vehicles, and methods for producing such compounds and for using such compounds in a new way especially for combating pests, e.g. fungi and bacteria, and for controlling plant growth, with other and further objects becoming apparent from a study of the within specification and accompanying examples.

It has been disclosed in German Published Specification DOS 2,201,063 that 1,2,4-triazole derivatives, such as, for example, 1-[1,2,4-triazolyl-(1)]-1-(4'-chlorophenoxy)-3,3-dimethyl-butan-2-one (Compound A), exhibit a good fungicidal activity. The effect of these compounds is not always entirely satisfactory if low amounts and low concentrations are used, and in particular is inadequate in the case of fungi other than mildews.

The present invention provides, as new compounds, the metal complexes of azolyl ethers of the general formula

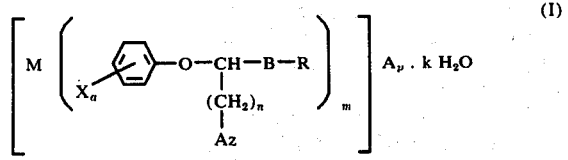

in which
M is a metal,
X is halogen, nitro, nitrile, optionally substituted alkyl, optionally substituted aryl, cycloalkyl, amino, carboxyl, alkoxycarbonyl, alkylcarbonyloxy, alkoxy, alkylthio, halogenoalkoxy, halogenoalkylthio, aryloxy, arylcarbonyloxy, benzoyl, halogenobenzoyl, alkylcarbonylamino, dialkylamino, alkylsulfonyl, alkylsulfonyloxy, arylsulfonyl or arylsulfonyloxy,
Az is an imidazolyl radical, a 1,2,4-triazolyl-(1) radical or a 1,2,4-triazolyl-(4) radical,
B is CO or CH(OH),
R is alkyl or optionally substituted aryl,
A is an anion of an inorganic acid,
$a$ is 0 or an integer from 1 to 5,
$n$ is 0 or 1,
$m$ is an integer from 1 to 4,
$p$ is an integer from 1 to 6, and
$k$ is an integer from 0 to 12.

Preferably X is halogen, nitrile, nitro, amino, alkyl or cycloalkyl with in either case up to 6 carbon atoms, halogenoalkyl with 1 or 2 carbon atoms and up to 5 halogen atoms (especially fluorine and chlorine atoms), hydroxymethyl, phenyl, halogenophenyl, (such as chlorophenyl, bromophenyl or fluorophenyl), phenyl-substituted phenyl, carboxyl, alkoxycarbonyl or alkylcarbonyloxy with in either case a total of up to 5 carbon atoms, alkoxy or alkylthio with in either case 1 or 2 carbon atoms, halogenoalkoxy or halogenoalkylthio with in either case 1 or 2 carbon atoms and up to 5 halogen atoms (especially fluorine and chlorine atoms), phenoxy, benzoyloxy, chlorophenoxy, chlorobenzoyloxy, benzoyl, chlorobenzoyl, dialkylamino with a total of up to 6 carbon atoms, alkylcarbonylamino with a total of up to 4 carbon atoms, alkylsulfonyl or alkylsulfonyloxy with in either case 1 or 2 carbon atoms, phenylsulfonyl and phenylsulfonyloxy; R is straight-chain or branched alkyl with 1 to 6 carbon atoms or an optionally o-substituted or p-substituted phenyl radical (preferred substituents being halogen, especially fluorine and chlorine, nitro, nitrile and methyl); $a$, is 0, 1, 2, 3 or 4; M is a metal of any of the sub-groups I, II and IV to VIII or a metal of the main group II or IV (especially copper, zinc, manganese, magnesium, tin, iron and nickel); A is a chloride, bromide, iodide, nitrate, sulfate or phosphate anion; $p$ is an integer from 1 to 4 and $k$ is an integer from 0 to 8.

Surprisingly, the metal complexes of azolyl ethers, according to the invention, exhibit a substantially greater fungicidal activity, especially against fungi responsible for leaf diseases and shoot diseases, than the triazolyl derivatives known from the state of the art which are the most closely related active compounds. The compounds according to the invention thus represent an enrichment of the art.

The invention also provides a process for the preparation of a metal complex of the formula (I) in which an azolyl ether of the general formula

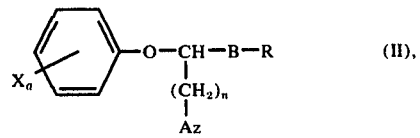

in which
X, Az, B, R, $a$ and $n$ have the above-mentioned meanings, is reacted with a metal salt of the general formula

in which
M, A, $p$ and $k$ have the above-mentioned meanings, in the presence of a solvent.

If 1-[1,2,4-triazolyl-(1)]-1-(p-chlorophenoxy)-3,3-dimethyl-butan-2-one and copper(II) chloride are used as starting materials, the course of the reaction can be represented by the following equation:

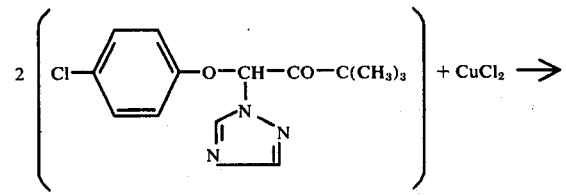

-continued

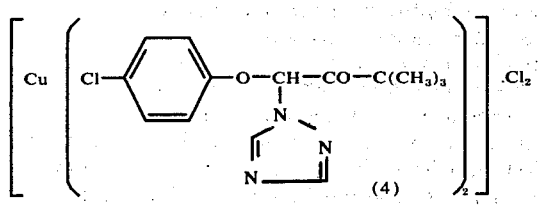

Some of the starting materials of the formula (II) are known. Those 1,2,4-triazole and imidazole derivatives of the formula (II), in which B represents the CO group and the index n represents 0, can inter alia be obtained by reaction of appropriately substituted halogenoether ketones with 1,2,4-triazoles or imidazoles in the presence of an acid-binding agent and, if appropriate, in the presence of a diluent according to German Published Specifications DOS 2,201,063 and 2,105,490. Other azolyl ethers of the formula (II) form the subject of Patent applications Ser. No. 510,833, filed Sept. 30, 1974, now U.S. Pat. No. 3,940,415, Ser. No. 509,881, filed Sept. 27, 1974, now pending, Ser. No. 480,433, filed June 17, 1974, now U.S. Pat. No. 3,940,414, and Ser. No. 465,713, filed Apr. 30, 1974, now U.S. Pat. No. 3,952,002, and German Published Specification DOS P 23 486 63, filed Sept. 9, 1973 and published March 1975.

Thus, those 1,2,4-triazole and imidazole derivatives of the formula (II) in which n is 1 and B is the CO group are obtained by reacting correspondingly substituted quaternary ammonium iodides with the desired azoles in the presence of solvents or diluents at temperatures between 20° and 150° C (see the preparative Examples hereinbelow).

The quaternary ammonium iodies which can be used also currently do not yet form part of the state of the art. They can be prepared by methylating, and quaternizing correspondingly substituted amines in accordance with customary methods. The amines themselves are in some cases known. They can be prepared according to customary methods, for example by Mannich reactions of ether ketones with formaldehyde and amine (see J. Am. Chem. Soc. 82 (1960), 1867–1872).

The corresponding triazole and imidazole derivatives, of the formula (II), in which B represents the CH(OH)— group, are obtained if the particular ketone derivatives (wherein B is CO in formula (II)) are reduced according to customary methods, for example with hydrogen in the presence of a catalyst and optionally in the presence of a polar solvent, or with complex hydrides, optionally in the presence of a polar solvent (see the preparative Examples hereinbelow).

Starting materials of the formula (II) which are still new can be prepared analogously to the general description given above.

The following may be mentioned (see Tables 1 and 2) as examples of the starting materials of the formula (II) which can be used in accordance with the invention:

Table 1

Starting materials, which can be used according to the invention, of the general formula $$\text{(IIa)}$$

| X | a | n | Y | B | R |
|---|---|---|---|---|---|
| 4-NH$_2$ | 1 | 0 | N | CO | C(CH$_3$)$_3$ |
| 3-Cl | 1 | 0 | N | CO | C(CH$_3$)$_3$ |
| 4-Br, 2-Cl | 2 | 0 | N | CO | C(CH$_3$)$_3$ |
| 2-OCH$_3$ | 1 | 0 | N | CO | C(CH$_3$)$_3$ |
| 2,4-CH$_3$ | 2 | 0 | N | CO | C(CH$_3$)$_3$ |
| 2,4,5-Cl | 3 | 0 | N | CO | C(CH$_3$)$_3$ |
| 2-CH$_3$, 5-Cl | 2 | 0 | N | CO | C(CH$_3$)$_3$ |
| 4-Cl, 3-CH$_3$ | 2 | 0 | N | CO | C(CH$_3$)$_3$ |
| 3,5-CH$_3$, 4-Cl | 3 | 0 | N | CO | C(CH$_3$)$_3$ |
| 3-CF$_3$ | 1 | 0 | N | CO | C(CH$_3$)$_3$ |
| 4-Cl | 1 | 0 | N | CO | CH$_3$ |
| 2,6-Cl | 2 | 0 | N | CO | 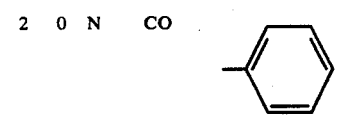 |
| 2,4-Cl | 2 | 0 | N | CO | 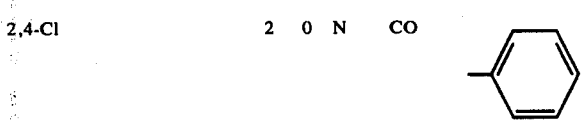 |

Table 1 -continued

Starting materials, which can be used according to the invention, of the general formula $$\text{X}_n\text{-C}_6\text{H}_{4-a}\text{-O-CH(-(CH}_2)_n\text{-N(imidazole-Y))-B-R} \quad \text{(IIa)}$$

| X | a | n | Y | B | R |
|---|---|---|---|---|---|
| 2-Br, 4-C₆H₅ | 2 | 0 | N | CO | C(CH₃)₃ |
| 3,4-Cl | 2 | 0 | N | CO | C(CH₃)₃ |
| 2-CH₃, 5-NO₂ | 2 | 0 | N | CO | C(CH₃)₃ |
| 3-Cl, 4-NO₂ | 2 | 0 | N | CO | C(CH₃)₃ |
| 4-Cl | 1 | 0 | N | CO | C(CH₃)₃ |
| 2,4-Cl | 2 | 0 | N | CO | C(CH₃)₃ |
| 4-NO₂ | 1 | 0 | N | CO | C(CH₃)₃ |
| 4-C(CH₃)₃ | 1 | 0 | N | CO | C(CH₃)₃ |
| 2,6-Cl | 2 | 0 | N | CO | C(CH₃)₃ |
| — | 0 | 0 | N | CO | C₆H₅ |
| 2,3-CH₃ | 2 | 0 | N | CO | C(CH₃)₃ |
| 3,4-CH₃ | 2 | 0 | N | CO | C(CH₃)₃ |
| 2,5-Cl | 2 | 0 | N | CO | C(CH₃)₃ |
| 4-Br | 1 | 0 | N | CO | C(CH₃)₃ |
| 4-F | 1 | 0 | N | CO | C(CH₃)₃ |
| 4-CH₃ | 1 | 0 | N | CO | C(CH₃)₃ |
| 4-CH(CH₃)₂ | 1 | 0 | N | CO | C(CH₃)₃ |
| 2-CH₃, 4-Cl | 2 | 0 | N | CO | C(CH₃)₃ |
| 4-CF₃ | 1 | 0 | N | CO | C(CH₃)₃ |
| 4-C₆H₅ | 1 | 0 | N | CO | C(CH₃)₃ |
| 2-C₆H₅ | 1 | 0 | N | CO | C(CH₃)₃ |
| 2-Cl | 1 | 0 | N | CO | C(CH₃)₃ |
| —O | 0 | N | CO | C(CH₃)₃ | |
| 2,4-Cl | 2 | 0 | N | CO | CH₃ |
| 2,4-Cl | 2 | 0 | N | CO | CH(CH₃)₂ |
| 2,4-Cl | 2 | 0 | N | CO | 4-Cl-C₆H₄ |
| 4 CH₃O—CO— | 1 | 0 | N | CO | C(CH₃)₃ |
| — | 0 | 0 | N | CO | C₆H₅ |
| 4-C₆H₁₁ (cyclohexyl) | 1 | 0 | N | CO | C(CH₃)₃ |
| 4-C₆H₄, 2-Cl | 2 | 0 | N | CO | C(CH₃)₃ |

Table 1 -continued

Starting materials, which can be used according to the invention, of the general formula

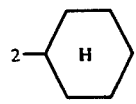
(IIa)

| X | a | n | Y | B | R |
|---|---|---|---|---|---|
|  2-cyclohexyl-H | 1 | 0 | N | CO | C(CH$_3$)$_3$ |
| 4-COOH | 1 | 0 | N | CO | C(CH$_3$)$_3$ |
| 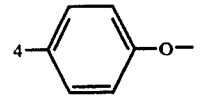 4-phenyl, 2,6-Cl | 3 | 0 | N | CO | C(CH$_3$)$_3$ |
| 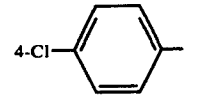 4-phenoxy | 1 | 0 | N | CO | C(CH$_3$)$_3$ |
| 2,4,6-Cl | 3 | 0 | N | CO | C(CH$_3$)$_3$ |
| 4-I | 1 | 0 | N | CO | C(CH$_3$)$_3$ |
| 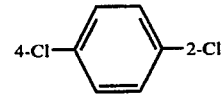 4-Cl-phenyl | 1 | 0 | N | CO | C(CH$_3$)$_3$ |
| 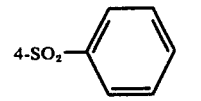 4-Cl-phenyl-2-Cl | 2 | 0 | N | CO | C(CH$_3$)$_3$ |
| 4-SO$_2$—CH$_3$ | 1 | 0 | N | CO | C(CH$_3$)$_3$ |
| 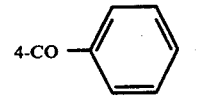 4-SO$_2$-phenyl | 1 | 0 | N | CO | C(CH$_3$)$_3$ |
| 4-CN | 1 | 0 | N | CO | C(CH$_3$)$_3$ |
| 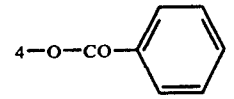 4-CO-phenyl | 1 | 0 | N | CO | C(CH$_3$)$_3$ |
| 4-O—SO$_2$—CH$_3$ | 1 | 0 | N | CO | C(CH$_3$)$_3$ |
| 4-OCF$_3$ | 1 | 0 | N | CO | C(CH$_3$)$_3$ |
| 4-O—CO—CH$_3$ | 1 | 0 | N | CO | C(CH$_3$)$_3$ |
| 4-O-CO-phenyl | 1 | 0 | N | CO | C(CH$_3$)$_3$ |
| 4-NH—COCH$_3$ | 1 | 0 | N | CO | C(CH$_3$)$_3$ |
| 4-OCH$_3$ | 1 | 0 | N | CO | C(CH$_3$)$_3$ |
| 3-NO$_2$ | 1 | 0 | N | CO | C(CH$_3$)$_3$ |
| 3-CN | 1 | 0 | N | CO | C(CH$_3$)$_3$ |
| 3-Br | 1 | 0 | N | CO | C(CH$_3$)$_3$ |
| 3-F | 1 | 0 | N | CO | C(CH$_3$)$_3$ |
| 3-OCH$_3$ | 1 | 0 | N | CO | C(CH$_3$)$_3$ |
| 3-CH$_3$ | 1 | 0 | N | CO | C(CH$_3$)$_3$ |
| 3-N(CH$_3$)$_2$ | 1 | 0 | N | CO | C(CH$_3$)$_3$ |
| 3-O—CO—CH$_3$ | 1 | 0 | N | CO | C(CH$_3$)$_3$ |

Table 1 -continued

Starting materials, which can be used according to the invention, of the general formula

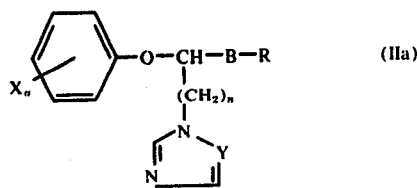

| X | a | n | Y | B | R |
|---|---|---|---|---|---|
| 3-O—CO—C₆H₅ | 1 | 0 | N | CO | C(CH₃)₃ |
| 2-NO₂ | 1 | 0 | N | CO | C(CH₃)₃ |
| 2-CN | 1 | 0 | N | CO | C(CH₃)₃ |
| 2-O—CO—CH₃ | 1 | 0 | N | CO | C(CH₃)₃ |
| 2-CH₃ | 1 | 0 | N | CO | C(CH₃)₃ |
| 2—O—CO—C₆H₅ | 1 | 0 | N | CO | C(CH₃)₃ |
| 2-F | 1 | 0 | N | CO | C(CH₃)₃ |
| 2-CO—C₆H₅ | 1 | 0 | N | CO | C(CH₃)₃ |
| 2-O—C₆H₅ | 1 | 0 | N | CO | C(CH₃)₃ |
| 4-Br | 1 | 1 | N | CO | C(CH₃)₃ |
| 4-F | 1 | 1 | N | CO | C(CH₃)₃ |
| 2-Cl | 1 | 1 | N | CO | C(CH₃)₃ |
| 3-Cl | 1 | 1 | N | CO | C(CH₃)₃ |
| 4-Cl | 1 | 1 | N | CO | C(CH₃)₃ |
| 4-CH₃ | 1 | 1 | N | CO | C(CH₃)₃ |
| 2-CH₃, 4-Cl | 2 | 1 | N | CO | C(CH₃)₃ |
| 2,5-Cl | 2 | 1 | N | CO | C(CH₃)₃ |
| 2,4-Cl | 2 | 1 | N | CO | C(CH₃)₃ |
| 2,3-CH₃ | 2 | 1 | N | CO | C(CH₃)₃ |
| 3,4-CH₃ | 2 | 1 | N | CO | C(CH₃)₃ |
| 2,4-CH₃ | 2 | 1 | N | CO | C(CH₃)₃ |
| 4-NO₂ | 1 | 1 | N | CO | C(CH₃)₃ |
| — | 0 | 1 | N | CO | C₆H₅ |
| — | 0 | 1 | N | CO | 4-Cl-C₆H₄ |
| 4-Cl | 1 | 1 | N | CO | 4-Cl-C₆H₄ |
| 4-Cl | 1 | 1 | N | CO | 4-Cl-C₆H₄ |

Table 1 -continued

Starting materials, which can be used according to the invention, of the general formula

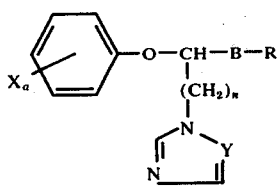
(IIa)

| X | a | n | Y | B | R |
|---|---|---|---|---|---|
| 2,4-Cl | 2 | 1 | N | CO | 4-Cl-C₆H₄- |
| 4-SO₂—CH₃ | 1 | 1 | N | CO | C(CH₃)₃ |
| 4-SO₂—C₆H₅ | 1 | 1 | N | CO | C(CH₃)₃ |
| 4-CN | 1 | 1 | N | CO | C(CH₃)₃ |
| 4-CO—C₆H₅ | 1 | 1 | N | CO | C(CH₃)₃ |
| 4-O—SO₂—CH₃ | 1 | 1 | N | CO | C(CH₃)₃ |
| 4-OCF₃ | 1 | 1 | N | CO | C(CH₃)₃ |
| 4-O—COCH₃ | 1 | 1 | N | CO | C(CH₃)₃ |
| 4-O—CO—C₆H₅ | 1 | 1 | N | CO | C(CH₃)₃ |
| 4-NH—COCH₃ | 1 | 1 | N | CO | C(CH₃)₃ |
| 4-OCH₃ | 1 | 1 | N | CO | C(CH₃)₃ |
| 4-NO₂ | 1 | 1 | N | CO | C(CH₃)₃ |
| 3-CN | 1 | 1 | N | CO | C(CH₃)₃ |
| 2,6-Cl | 3 | | | | |
| 3-Br | 1 | 1 | N | CO | C(CH₃)₃ |
| 3-F | 1 | 1 | N | CO | C(CH₃)₃ |
| 3-OCH₃ | 1 | 1 | N | CO | C(CH₃)₃ |
| 2-C; 3-CH3 4-Cl | 1 | 1 | N | CO | C(CH₃)₃ |
| 3-N(CH₃)₂ | 1 | 1 | N | CO | C(CH₃)₃ |
| 3-O—CO—C₆H₅ | 1 | 1 | N | CO | C(CH₃)₃ |
| 3-O—CO—CH₃ | 1 | 1 | N | CO | C(CH₃)₃ |
| 2-NO₂ | 1 | 1 | N | CO | C(CH₃)₃ |
| 2-CN | 1 | 1 | N | CO | C(CH₃)₃ |
| 2-O—CO—CH₃ | 1 | 1 | N | CO | C(CH₃)₃ |
| 4-Cl | 1 | 1 | N | CO | C₆H₅- |
| 2-CH₃ | 1 | 1 | N | CO | C(CH₃)₃ |
| 2-O—CO—C₆H₅ | 1 | 1 | N | CO | C(CH₃)₃ |
| 2-F | 1 | 1 | N | CO | C(CH₃)₃ |

Table 1 -continued

Starting materials, which can be used according to the invention, of the general formula

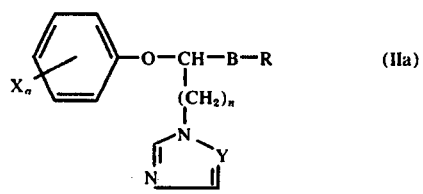

(IIa)

| X | a | n | Y | B | R |
|---|---|---|---|---|---|
| 2-CO-C₆H₅ | 1 | 1 | N | CO | C(CH₃)₃ |
| 2-O-C₆H₅ | 1 | 1 | N | CO | C(CH₃)₃ |
| 3-Cl | 1 | 0 | CH | CO | C(CH₃)₃ |
| 2,6-Cl | 2 | 0 | CH | CO | C(CH₃)₃ |
| 2,5-Cl | 2 | 0 | CH | CO | C(CH₃)₃ |
| 2,4-Cl | 2 | 0 | CH | CO | C(CH₃)₃ |
| 2-Cl | 1 | 0 | CH | CO | C(CH₃)₃ |
| 4-Cl | 1 | 0 | CH | CO | C(CH₃)₃ |
| 4-C₆H₅, 2,6-Cl | 3 | 0 | CH | CO | C(CH₃)₃ |
| 4-C₆H₅, 2-Cl | 2 | 0 | CH | CO | C(CH₃)₃ |
| 4-Cl-C₆H₄ | 1 | 0 | CH | CO | C(CH₃)₃ |
| 2-Br, 4-Cl | 2 | 0 | CH | CO | C(CH₃)₃ |
| 4-Br | 0 | CH | CO | C(CH₃)₃ | |
| — | 0 | 0 | CH | CO | C(CH₃)₃ |
| 4-C₆H₅ | 1 | 0 | CH | CO | C(CH₃)₃ |
| 3-Cl, 4-NO₂ | 2 | 0 | CH | CO | C(CH₃)₃ |
| 2-CH₃, 5-NO₂ | 2 | 0 | CH | CO | C(CH₃)₃ |
| 4-NH₂ | 1 | 0 | CH | CO | C(CH₃)₃ |
| 2-C₆H₅ | 1 | 0 | CH | CO | C(CH₃)₃ |
| 2-Cl, 6-C₆H₅ | 2 | 0 | CH | CO | C(CH₃)₃ |
| 4-NO₂ | 1 | 0 | CH | CO | C(CH₃)₃ |
| 4-F | 1 | 0 | CH | CO | C(CH₃)₃ |
| 4-C(CH₃)₃ | 1 | 0 | CH | CO | C(CH₃)₃ |
| 2,4,6-Cl | 3 | 0 | CH | CO | C₆H₅ |

Table 1 -continued
Starting materials, which can be used according to the invention, of the general formula
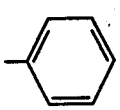 (IIa)
| X | a | n | Y | B | R |
|---|---|---|---|---|---|
| 2-Cl | 1 | 0 | CH | CO | C(CH$_3$)$_3$ |
| 3-Cl | 1 | 0 | CH | CO | C(CH$_3$)$_3$ |
| — | 0 | 0 | CH | CO | C(CH$_3$)$_3$ |
| 2,4,5-Cl | 3 | 0 | CH | CO | 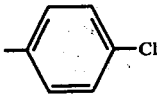 |
| 2,6-Cl | 2 | 0 | CH | CO | C(CH$_3$)$_3$ |
| 2,4-Cl | 2 | 0 | CH | CO | 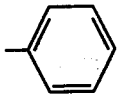 |
| 2,4-Cl | 2 | 0 | CH | CO | CH$_3$ |
| — | 0 | 0 | CH | CO | 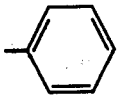 |
| 2-Cl | 1 | 0 | CH | CO | 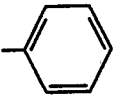 |
| 3-Cl | 1 | 0 | CH | CO | 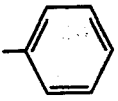 |
| 4-Cl | 1 | 0 | CH | CO | 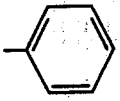 |
| 2,4-Cl | 2 | 0 | CH | CO | 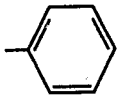 |
| 2,6-Cl | 2 | 0 | CH | CO | 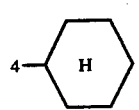 |
| 4-Br, 2-Cl | 2 | 0 | CH | CO | C(CH$_3$)$_3$ |
| 4-H (cyclohexyl) | 1 | 0 | CH | CO | C(CH$_3$)$_3$ |
| 4-I | 1 | 0 | CH | CO | C(CH$_3$)$_3$ |
| 4-COOH | 1 | 0 | CH | CO | C(CH$_3$)$_3$ |
| 4-SO$_2$—CH$_3$ | 1 | 0 | CH | CO | C(CH$_3$)$_3$ |

Table 1 -continued

Starting materials, which can be used according to the invention, of the general formula $$\text{X}_a\text{-C}_6\text{H}_{4-a}\text{-O-CH(-(CH}_2)_n\text{-N(imidazole-Y))-B-R}$$ (IIa)

| X | a | n | Y | B | R |
|---|---|---|---|---|---|
| 4-SO$_2$-C$_6$H$_5$ | 1 | 0 | CH | CO | C(CH$_3$)$_3$ |
| 4-CN | 1 | 0 | CH | CO | C(CH$_3$)$_3$ |
| 4-CO-C$_6$H$_5$ | 1 | 0 | CH | CO | C(CH$_3$)$_3$ |
| 4-H$_5$C$_2$O—CO— | 1 | 0 | CH | CO | C(CH$_3$)$_3$ |
| 4-O—SO$_2$—CH$_3$ | 1 | 0 | CH | CO | C(CH$_3$)$_3$ |
| 4-OCF$_3$ | 1 | 0 | CH | CO | C(CH$_3$)$_3$ |
| 4-O—CO—CH$_3$ | 1 | 0 | CH | CO | C(CH$_3$)$_3$ |
| 4-O—CO-C$_6$H$_5$ | 1 | 0 | CH | CO | C(CH$_3$)$_3$ |
| 4-NH—COCH$_3$ | 1 | 0 | CH | CO | C(CH$_3$)$_3$ |
| 4-OCH$_3$ | 1 | 0 | CH | CO | C(CH$_3$)$_3$ |
| 3-NO$_2$ | 1 | 0 | CH | CO | C(CH$_3$)$_3$ |
| 3-CN | 1 | 0 | CH | CO | C(CH$_3$)$_3$ |
| 3-Br | 1 | 0 | CH | CO | C(CH$_3$)$_3$ |
| 3-F | 1 | 0 | CH | CO | C(CH$_3$)$_3$ |
| 3-OCH$_3$ | 1 | 0 | CH | CO | C(CH$_3$)$_3$ |
| 3-CH$_3$ | 1 | 0 | CH | CO | C(CH$_3$)$_3$ |
| 3-N(CH$_3$)$_2$ | 1 | 0 | CH | CO | C(CH$_3$)$_3$ |
| 3-O—CO—CH$_3$ | 1 | 0 | CH | CO | C(CH$_3$)$_3$ |
| 3-O—CO-C$_6$H$_5$ | 1 | 0 | CH | CO | C(CH$_3$)$_3$ |
| 2-NO$_2$ | 1 | 0 | CH | CO | C(CH$_3$)$_3$ |
| 2-CN | 1 | 0 | CH | CO | C(CH$_3$)$_3$ |
| 2-O—CO—CH$_3$ | 1 | 0 | CH | CO | C(CH$_3$)$_3$ |
| 2-CH$_3$ | 1 | 0 | CH | CO | C(CH$_3$)$_3$ |
| 2-O—CO-C$_6$H$_5$ | 1 | 0 | CH | CO | C(CH$_3$)$_3$ |
| 2-F | 1 | 0 | CH | CO | C(CH$_3$)$_3$ |
| 2-CO-C$_6$H$_5$ | 1 | 0 | CH | CO | C(CH$_3$)$_3$ |
| 2-O-C$_6$H$_5$ | 1 | 0 | CH | CO | C(CH$_3$)$_3$ |
| 4-CL | 1 | 1 | CH | CO | C(CH$_3$)$_3$ |
| 2,5-CL | 2 | 1 | CH | CO | C(CH$_3$)$_3$ |
| — | 0 | 1 | CH | CO | C(CH$_3$)$_3$ |
| 2,4-CL | 2 | 1 | CH | CO | C(CH$_3$)$_3$ |
| 4-Br | 1 | 1 | CH | CO | C(CH$_3$)$_3$ |
| 4-F | 1 | 1 | CH | CO | C(CH$_3$)$_3$ |
| 2-Cl | 1 | 1 | CH | CO | C(CH$_3$)$_3$ |

Table 1 -continued

Starting materials, which can be used according to the invention, of the general formula

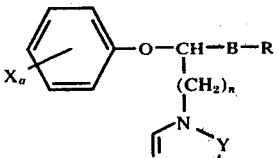

(IIa)

| X | a | n | Y | B | R |
|---|---|---|---|---|---|
| 3-Cl | 1 | 1 | CH | CO | $C(CH_3)_3$ |
| 4-$CH_3$ | 1 | 1 | CH | CO | $C(CH_3)_3$ |
| 2-$CH_3$, 4-Cl | 2 | 1 | CH | CO | $C(CH_3)_3$ |
|  | 1 | 1 | CH | CO | $C(CH_3)_3$ |
| 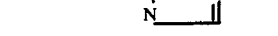 | 1 | 1 | CH | CO | $C(CH_3)_3$ |
| 2,3-$CH_3$ | 2 | 1 | CH | CO | $C(CH_3)_3$ |
| 3,4-$CH_3$ | 2 | 1 | CH | CO | $C(CH_3)_3$ |
| 2,4-$CH_3$ | 2 | 1 | CH | CO | $C(CH_3)_3$ |
| 4,$NO_2$ | 1 | 1 | CH | CO | $C(CH_3)_3$ |
| 4-$NO_2$, 2-CL | 2 | 1 | CH | CO | $C(CH_3)_3$ |
| 2-Cl, 5-$NO_2$ | 2 | 1 | CH | CO | $C(CH_3)_3$ |
| 2,4,5-Cl | 3 | 1 | CH | CO | $C(CH_3)_3$ |
|  | 2 | 1 | CH | CO | $C(CH_3)_3$ |
| 4-Cl | 1 | 1 | CH | CO |  |
| — | 0 | 1 | CH | CO |  |
| 4-Cl | 1 | 1 | CH | CO |  |
| 4-Cl | 1 | 1 | CH | CO |  |
| 2,4-Cl | 2 | 1 | CH | CO | 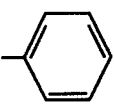 |
|  | 1 | 1 | CH | CO | $C(CH_3)_3$ |
| 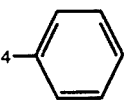 | 2 | 1 | CH | CO | $C(CH_3)_3$ |

Table 1 -continued

Starting materials, which can be used according to the invention, of the general formula

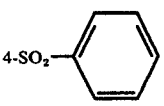

| X | a | n | Y | B | R |
|---|---|---|---|---|---|
| 4-SO$_2$CH$_3$ | 1 | 1 | CH | CO | C(CH$_3$)$_3$ |
| 4-SO$_2$-C$_6$H$_5$ | 1 | 1 | CH | CO | C(CH$_3$)$_3$ |
| 4-CN | 1 | 1 | CH | CO | C(CH$_3$)$_3$ |
| 4-CO-C$_6$H$_5$ | 1 | 1 | CH | CO | C(CH$_3$)$_3$ |
| 4-O—SO$_2$—CH$_3$ | 1 | 1 | CH | CO | C(CH$_3$)$_3$ |
| 4-OCF$_3$ | 1 | 1 | CH | CO | C(CH$_3$)$_3$ |
| 4-O—CO—CH$_3$ | 1 | 1 | CH | CO | C(CH$_3$)$_3$ |
| 4-O—CO—C$_6$H$_5$ | 1 | 1 | CH | CO | C(CH$_3$)$_3$ |
| 4-NH—COCH$_3$ | 1 | 1 | CH | CO | C(CH$_3$)$_3$ |
| 4-OCH$_3$ | 1 | 1 | CH | CO | C(CH$_3$)$_3$ |
| 3-NO$_2$ | 1 | 1 | CH | CO | C(CH$_3$)$_3$ |
| 3-CN | 1 | 1 | CH | CO | C(CH$_3$)$_3$ |
| 3-Br | 1 | 1 | CH | CO | C(CH$_3$)$_3$ |
| 3-F | 1 | 1 | CH | CO | C(CH$_3$)$_3$ |
| 3-OCH$_3$ | 1 | 1 | CH | CO | C(CH$_3$)$_3$ |
| 3-CH$_3$ | 1 | 1 | CH | CO | C(CH$_3$)$_3$ |
| 3-N(CH$_3$)$_2$ | 1 | 1 | CH | CO | C(CH$_3$)$_3$ |
| 3-O—CO—CH$_3$ | 1 | 1 | CH | CO | C(CH$_3$)$_3$ |
| 3-O—CO—C$_6$H$_5$ | 1 | 1 | CH | CO | C(CH$_3$)$_3$ |
| 3-NO$_2$ | 1 | 1 | CH | CO | C(CH$_3$)$_3$ |
| 2-CN | 1 | 1 | CH | CO | C(CH$_3$)$_3$ |
| 2-O—CO—CH$_3$ | 1 | 1 | CH | CO | C(CH$_3$)$_3$ |
| 2-CH$_3$ | 1 | 1 | CH | CO | C(CH$_3$)$_3$ |
| 2-O—CO—C$_6$H$_5$ | 1 | 1 | CH | CO | C(CH$_3$)$_3$ |
| 2-F | 1 | 1 | CH | CO | C(CH$_3$)$_3$ |
| 2-CO—C$_6$H$_5$ | 1 | 1 | CH | CO | C(CH$_3$)$_3$ |
| 2-O—C$_6$H$_5$ | 1 | 1 | CH | CO | C(CH$_3$)$_3$ |
| 3-Cl | 1 | 0 | CH | CHOH | C(CH$_3$)$_3$ |
| 4-Cl | 1 | 0 | CH | CHOH | C(CH$_3$)$_3$ |
| 4-Br | 1 | 0 | CH | CHOH | C(CH$_3$)$_3$ |
| 4-F | 1 | 0 | CH | CHOH | C(CH$_3$)$_3$ |
| 2,4-Cl | 2 | 0 | CH | CHOH | C(CH$_3$)$_3$ |
| 2,6-Cl | 2 | 0 | CH | CHOH | C(CH$_3$)$_3$ |

Table 1 -continued

Starting materials, which can be used according to the invention, of the general formula

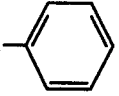 (IIa)

| X | a | n | Y | B | R |
|---|---|---|---|---|---|
| 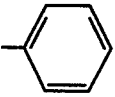 2- | 1 | 0 | CH | CHOH | C(CH$_3$)$_3$ |
| 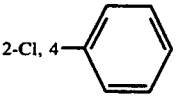 4- | 1 | 0 | CH | CHOH | C(CH$_3$)$_3$ |
| 4-C(CH$_3$)$_3$ | 1 | 0 | CH | CHOH | C(CH$_3$)$_3$ |
| 2-Cl, 4- 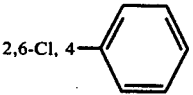 | 2 | 0 | CH | CHOH | C(CH$_3$)$_3$ |
| 2,6-Cl, 4-  | 3 | 0 | CH | CHOH | C(CH$_3$)$_3$ |
| — | 0 | 0 | CH | CHOH | C(CH$_3$)$_3$ |
| 4—  H | 1 | 0 | CH | CHOH | C(CH$_3$)$_3$ |
| 2— 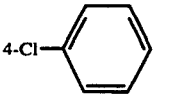 H | 1 | 0 | CH | CHOH | C(CH$_3$)$_3$ |
| 4-Cl— 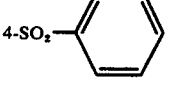 | 1 | 0 | CH | CHOH | C(CH$_3$)$_3$ |
| 4-I | 1 | 0 | CH | CHOH | C(CH$_3$)$_3$ |
| 4-SO$_2$—CH$_3$ | 1 | 0 | CH | CHOH | C(CH$_3$)$_3$ |
| 4-SO$_2$— 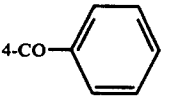 | 1 | 0 | CH | CHOH | C(CH$_3$)$_3$ |
| 4-CN | 1 | 0 | CH | CHOH | C(CH$_3$)$_3$ |
| 4-CO— 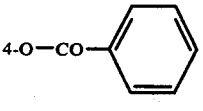 | 1 | 0 | CH | CHOH | C(CH$_3$)$_3$ |
| 4-O—SO$_2$—CH$_3$ | 1 | 0 | CH | CHOH | C(CH$_3$)$_3$ |
| 4-OCF$_3$ | 1 | 0 | CH | CHOH | C(CH$_3$)$_3$ |
| 4-O—CO—CH$_3$ | 1 | 0 | CH | CHOH | C(CH$_3$)$_3$ |
| 4-O—CO— | 1 | 0 | CH | CHOH | C(CH$_3$)$_3$ |
| 4-NH-COCH$_3$ | 1 | 0 | CH | CHOH | C(CH$_3$)$_3$ |

Table 1 -continued

Starting materials, which can be used according to the invention, of the general formula

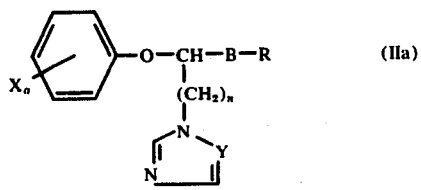

(IIa)

| X | a | n | Y | B | R |
|---|---|---|---|---|---|
| 4-OCH$_3$ | 1 | 0 | CH | CHOH | C(CH$_3$)$_3$ |
| 3-NO$_2$ | 1 | 0 | CH | CHOH | C(CH$_3$)$_3$ |
| 3-CN | 1 | 0 | CH | CHOH | C(CH$_3$)$_3$ |
| 3-Br | 1 | 0 | CH | CHOH | C(CH$_3$)$_3$ |
| 3-F | 1 | 0 | CH | CHOH | C(CH$_3$)$_3$ |
| 3-OCH$_3$ | 1 | 0 | CH | CHOH | C(CH$_3$)$_3$ |
| 3-CH$_3$ | 1 | 0 | CH | CHOH | C(CH$_3$)$_3$ |
| 3-N(CH$_3$)$_2$ | 1 | 0 | CH | CHOH | C(CH$_3$)$_3$ |
| 3-O—CO—CH$_3$ | 1 | 0 | CH | CHOH | C(CH$_3$)$_3$ |
| 3-O—CO—C$_6$H$_5$ | 1 | 0 | CH | CHOH | C(CH$_3$)$_3$ |
| 3,2 | | | | | |
| 2-CN | 1 | 0 | CH | CHOH | C(CH$_3$)$_3$ |
| 2-O—CO—CH$_3$ | 1 | 0 | CH | CHOH | C(CH$_3$)$_3$ |
| 2-CH$_3$ | 1 | 0 | CH | CHOH | C(CH$_3$)$_3$ |
| 2-O—CO—C$_6$H$_5$ | 1 | 0 | CH | CHOH | C(CH$_3$)$_3$ |
| 2-F | 1 | 0 | CH | CHOH | C(CH$_3$)$_3$ |
| 2-CO—C$_6$H$_5$ | 1 | 0 | CH | CHOH | C(CH$_3$)$_3$ |
| 2-O—C$_6$H$_5$ | 1 | 0 | CH | CHOH | C(CH$_3$)$_3$ |
| 4-NO$_2$ | 1 | 0 | N | CHOH | C(CH$_3$)$_3$ |
| 4-C(CH$_3$)$_3$ | 1 | 0 | N | CHOH | C(CH$_3$)$_3$ |
| 4-CH$_3$ | 1 | 0 | N | CHOH | C(CH$_3$)$_3$ |
| 2-Cl | 1 | 0 | N | CHOH | C(CH$_3$)$_3$ |
| 3-Cl | 1 | 0 | N | CHOH | C(CH$_3$)$_3$ |
| — | 0 | 0 | N | CHOH | C(CH$_3$)$_3$ |
| 4-Cl | 1 | 0 | N | CHOH | C(CH$_3$)$_3$ |
| 4-Cl | 1 | 0 | N | CHOH | CH$_3$ |
| 4-Cl | 1 | 0 | N | CHOH | C$_6$H$_5$ |
| 4-Br | 1 | 0 | N | CHOH | C(CH$_3$)$_3$ |
| 4-F | 1 | 0 | N | CHOH | C(CH$_3$)$_3$ |
| 4-C$_6$H$_5$ | 1 | 0 | N | CHOH | C(CH$_3$)$_3$ |
| 2-C$_6$H$_5$ | 1 | 0 | N | CHOH | C(CH$_3$)$_3$ |
| 2,4-Cl | 2 | 0 | N | CHOH | C(CH$_3$)$_3$ |

Table 1 -continued

Starting materials, which can be used according to the invention, of the general formula $$X_a\text{-}C_6H_{?}\text{-}O\text{-}CH(\text{-}B\text{-}R)\text{-}(CH_2)_n\text{-}N(\text{imidazole-}Y)$$ (IIa)

| X | a | n | Y | B | R |
|---|---|---|---|---|---|
| 2-CH₃, 4-Cl | 2 | 0 | N | CHOH | C(CH₃)₃ |
| 3,4-CH₃ | 2 | 0 | N | CHOH | C(CH₃)₃ |
| 2,4,5-Cl | 3 | 0 | N | CHOH | C(CH₃)₃ |
| 4-CO—O—CH₃ | 1 | 0 | N | CHOH | C(CH₃)₃ |
| 4-(C₆H₃), 2,6-Cl | 3 | 0 | N | CHOH | C(CH₃)₃ |
| 2-Cl, 4-(C₆H₅) | 2 | 0 | N | CHOH | C(CH₃)₃ |
| 4-Cl-(C₆H₄)- | 1 | 0 | N | CHOH | C(CH₃)₃ |
| 2-(C₆H₁₁) | 1 | 0 | N | CHOH | C(CH₃)₃ |
| 4-(C₆H₁₁) | 1 | 0 | N | CHOH | C(CH₃)₃ |
| 2,4,6-Cl | 3 | 0 | N | CHOH | C(CH₃)₃ |
| 4-I | 1 | 0 | N | CHOH | C(CH₃)₃ |
| 4-SO₂—CH₃ | 1 | 0 | N | CHOH | C(CH₃)₃ |
| 4-CN | 1 | 0 | N | CHOH | C(CH₃)₃ |
| 4-SO₂-(C₆H₅) | 1 | 0 | N | CHOH | C(CH₃)₃ |
| 4-CO-(C₆H₅) | 1 | 0 | N | CHOH | C(CH₃)₃ |
| 4-O—SO₂—CH₃ | 1 | 0 | N | CHOH | C(CH₃)₃ |
| 4-CCF | 1 | 0 | N | CHOH | C(CH₃)₃ |
| 4-O—CO—CH₃ | 1 | 0 | N | CHOH | C(CH₃)₃ |
| 4-O—CO-(C₆H₅) | 1 | 0 | N | CHOH | C(CH₃)₃ |
| 4-NH—COCH₃ | 1 | 0 | N | CHOH | C(CH₃)₃ |
| 4-OCH₃ | 1 | 0 | N | CHOH | C(CH₃)₃ |
| 3-NO₂ | 1 | 0 | N | CHOH | C(CH₃)₃ |
| 3-CN | 1 | 0 | N | CHOH | C(CH₃)₃ |
| 3-Br | 1 | 0 | N | CHOH | C(CH₃)₃ |
| 3-F | 1 | 0 | N | CHOH | C(CH₃)₃ |
| 3-OCH₃ | 1 | 0 | N | CHOH | C(CH₃)₃ |
| 3-CH₃ | 1 | 0 | N | CHOH | C(CH₃)₃ |
| 3-N(CH₃)₂ | 1 | 0 | N | CHOH | C(CH₃)₃ |
| 3-O—CO—CH₃ | 1 | 0 | N | CHOH | C(CH₃)₃ |

Table 1 -continued

Starting materials, which can be used according to the invention, of the general formula

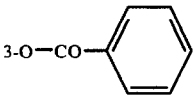 (IIa)

| X | a | n | Y | B | R |
|---|---|---|---|---|---|
| 3-O—CO—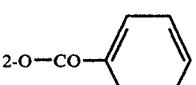 | 1 | 0 | N | CHOH | C(CH$_3$)$_3$ |
| 2-NO$_2$ | 1 | 0 | N | CHOH | C(CH$_3$)$_3$ |
| 2-CN | 1 | 0 | N | CHOH | C(CH$_3$)$_3$ |
| 2-O—CO—CH$_3$ | 1 | 0 | N | CHOH | C(CH$_3$)$_3$ |
| 2-CH$_3$ | 1 | 0 | N | CHOH | C(CH$_3$)$_3$ |
| 2-O—CO—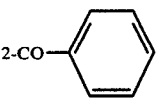 | 1 | 0 | N | CHOH | C(CH$_3$)$_3$ |
| 2-F | 1 | 0 | N | CHOH | C(CH$_3$)$_3$ |
| 2-CO—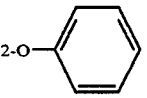 | 1 | 2 | 0 | N | CHOHC(CH$_3$)$_3$ |
| 2-O— | 1 | 0 | N | CHOH | C(CH$_3$)$_3$ |
| 2-CH$_3$, 4-Cl | 1 | 0 | N | CHOH | C(CH$_3$)$_3$ |
| 4-Cl | 2 | 1 | N | CHOH | C(CH$_3$)$_3$ |
| 2-Cl | 1 | 1 | N | CHOH | C(CH$_3$)$_3$ |
| 3-Cl | 1 | 1 | N | CHOH | C(CH$_3$)$_3$ |
| 2,4-Cl | 2 | 1 | N | CHOH | C(CH$_3$)$_3$ |
| 2,5-Cl | 2 | 1 | N | CHOH | C(CH$_3$)$_3$ |
| 2,3-CH$_3$ | 2 | 1 | N | CHOH | C(CH$_3$)$_3$ |
| 4-F | 1 | 1 | N | CHOH | C(CH$_3$)$_3$ |
| — | 0 | 1 | N | CHOH | C(CH$_3$)$_3$ |
| 2,4-Cl | 2 | 1 | N | CHOH | 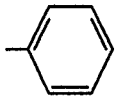 |
| — | 0 | 1 | N | CHOH | 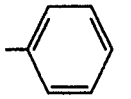 |
| 4-Cl | 1 | 1 | N | CHOH | 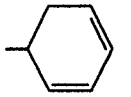 |
| 4-Cl | 1 | 1 | N | CHOH | 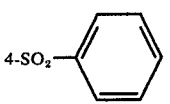 |
| 4-SO$_2$CH$_3$ | 1 | 1 | N | CHOH | C(CH$_3$)$_3$ |
| 4-SO$_2$— | 1 | 1 | N | CHOH | C(CH$_3$)$_3$ |

Table 1 -continued

Starting materials, which can be used according to the invention, of the general formula $$X_a\text{-}\langle\text{phenyl}\rangle\text{-O-CH-B-R} \quad \text{(IIa)}$$
with $(CH_2)_n$ and N-containing heterocycle (N=, Y)

| X | a | n | Y | B | R |
|---|---|---|---|---|---|
| 4-CN | 1 | 1 | N | CHOH | C(CH₃)₃ |
| 4-CO—⟨phenyl⟩ | 1 | 1 | N | CHOH | C(CH₃)₃ |
| 4-O—SO₂—CH₃ | 1 | 1 | N | CHOH | C(CH₃)₃ |
| 4-OCF₃ | 1 | 1 | N | CHOH | C(CH₃)₃ |
| 4-O—CO—CH₃ | 1 | 1 | N | CHOH | C(CH₃)₃ |
| 4-O—CO—⟨phenyl⟩ | 1 | 1 | N | CHOH | C(CH₃)₃ |
| 4-NH—COCH₃ | 1 | 1 | N | CHOH | C(CH₃)₃ |
| 4-OCH₃ | 1 | 1 | N | CHOH | C(CH₃)₃ |
| 3-NO₂ | 1 | 1 | N | CHOH | C(CH₃)₃ |
| 3-CN | 1 | 1 | N | CHOH | C(CH₃)₃ |
| 3-Br | 1 | 1 | N | CHOH | C(CH₃)₃ |
| 3-F | 1 | 1 | N | CHOH | C(CH₃)₃ |
| 3-OCH₃ | 1 | 1 | N | CHOH | C(CH₃)₃ |
| 3-CH₃ | 1 | 1 | N | CHOH | C(CH₃)₃ |
| 3-N(CH₃)₂ | 1 | 1 | N | CHOH | C(CH₃)₃ |
| 3-O—CO—CH₃ | 1 | 1 | N | CHOH | C(CH₃)₃ |
| 3-O—CO—⟨phenyl⟩ | 1 | 1 | N | CHOH | C(CH₃)₃ |
| 2-NO₂ | 1 | 1 | N | CHOH | C(CH₃)₃ |
| 2-CN | 1 | 1 | N | CHOH | C(CH₃)₃ |
| 2-O—CO—CH₃ | 1 | 1 | N | CHOH | C(CH₃)₃ |
| 2-CH₃ | 1 | 1 | N | CHOH | C(CH₃)₃ |
| 2-O—CO—⟨phenyl⟩ | 1 | 1 | N | CHOH | C(CH₃)₃ |
| 2-O—⟨phenyl⟩ | 1 | 1 | N | CHOH | C(CH₃)₂ |
| 2-CO—⟨phenyl⟩ | 1 | 1 | N | CHOH | C(CH₃)₃ |
| 2-F | 1 | 1 | N | CHOH | C(CH₃)₃ |
| 4-Cl | 1 | 1 | CH | CHOH | C(CH₃)₃ |
| 2-Cl | 1 | 1 | CH | CHOH | C(CH₃)₃ |
| 3-Cl | 1 | 1 | CH | CHOH | C(CH₃)₃ |
| 2,4-Cl | 2 | 1 | CH | CHOH | C(CH₃)₃ |
| 4-F | 1 | 1 | CH | CHOH | C(CH₃)₃ |
| 2-CH₃, 4-Cl | 2 | 1 | CH | CHOH | C(CH₃)₃ |
| — | 0 | 1 | CH | CHOH | C(CH₃)₃ |
| 4-Cl | 1 | 1 | CH | CHOH | 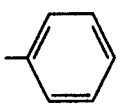 |

Table 1 -continued

Starting materials, which can be used according to the invention, of the general formula

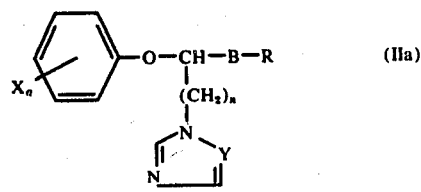

| X | a | n | Y | B | R |
|---|---|---|---|---|---|
| — | 0 | 1 | CH | CHOH | ⌬ |
| 4-Cl | 1 | 1 | CH | CHOH | ⌬-Cl |
| 2,4-Cl | 2 | 1 | CH | CHOH | ⌬-Cl |
| 4-SO$_2$—CH$_3$ | 1 | 1 | CH | CHOH | C(CH$_3$)$_3$ |
| 4-SO$_2$—⌬ | 1 | 1 | CH | CHOH | C(CH$_3$)$_3$ |
| 4-CN | 1 | 1 | CH | CHOH | C(CH$_3$)$_3$ |
| 4-CO—⌬ | 1 | 1 | CH | CHOH | C(CH$_3$)$_3$ |
| 4-O—SO$_2$—CH$_3$ | 1 | 1 | CH | CHOH | C(CH$_3$)$_3$ |
| 4-OCF$_3$ | 1 | 1 | CH | CHOH | C(CH$_3$)$_3$ |
| 4-O—CO—CH$_3$ | 1 | 1 | CH | CHOH | C(CH$_3$)$_3$ |
| 4-O—CO—⌬ | 1 | 1 | CH | CHOH | C(CH$_3$)$_3$ |
| 4-NH—COCH$_3$ | 1 | 1 | CH | CHOH | C(CH$_3$)$_3$ |
| 3-NO$_2$ | 1 | 1 | CH | CHOH | C(CH$_3$)$_3$ |
| 3-CN | 1 | 1 | CH | CHOH | C(CH$_3$)$_3$ |
| 3-Br | 1 | 1 | CH | CHOH | C(CH$_3$)$_3$ |
| 3-F | 1 | 1 | CH | CHOH | C(CH$_3$)$_3$ |
| 3-OCH$_3$ | 1 | 1 | CH | CHOH | C(CH$_3$)$_3$ |
| 3-CH$_3$ | 1 | 1 | CH | CHOH | C(CH$_3$)$_3$ |
| 3-N(CH$_3$)$_2$ | 1 | 1 | CH | CHOH | C(CH$_3$)$_3$ |
| 3-O—CO—CH$_3$ | 1 | 1 | CH | CHOH | C(CH$_3$)$_3$ |
| 3-O—CO—⌬ | 1 | 1 | CH | CHOH | C(CH$_3$)$_3$ |
| 2-NO$_2$ | 1 | 1 | CH | CHOH | C(CH$_3$)$_3$ |
| 2-CN | 1 | 1 | CH | CHOH | C(CH$_3$)$_3$ |
| 2-O—CO—CH$_3$ | 1 | 1 | CH | CHOH | C(CH$_3$)$_3$ |
| 2-CH$_3$ | 1 | 1 | CH | CHOH | C(CH$_3$)$_3$ |
| 2-O—CO—⌬ | 1 | 1 | CH | CHOH | C(CH$_3$)$_3$ |
| 2-F | 1 | 1 | CH | CHOH | C(CH$_3$)$_3$ |

Table 1 -continued

Starting materials, which can be used according to the invention, of the general formula $$\text{X}_a\text{-C}_6\text{H}_{4-a}\text{-O-CH(B-R)-(CH}_2)_n\text{-N(imidazole-Y)}$$ (IIa)

| X | a | n | Y | B | R |
|---|---|---|---|---|---|
| 2-CO-C₆H₅ | 1 | 1 | CH | CHOH | C(CH₃)₃ |
| 2-O-C₆H₅ | 1 | 1 | CH | CHOH | C(CH₃)₃ |

Table 2

Compounds, which can be used according to the invention, of the general formula $$\text{X}_a\text{-C}_6\text{H}_{4-a}\text{-O-CH(B-R)-(CH}_2)_n\text{-N(triazole)}$$ (IIb)

| X | a | n | B | R |
|---|---|---|---|---|
| 4-Br | 1 | 0 | CO | C(CH₃)₃ |
| 2,4-Cl | 2 | 0 | CO | C(CH₃)₃ |
| 4-C₆H₅ | 1 | 0 | CO | C(CH₃)₃ |
| 4-(4-Cl-C₆H₄) | 1 | 0 | CO | C(CH₃)₃ |
| 2,4,5-Cl | 3 | 0 | CO | C(CH₃)₃ |
| 2,4,6-Cl | 3 | 0 | CO | C(CH₃)₃ |
| 2,4-Cl | 2 | 0 | CHOH | C(CH₃)₃ |

The metal salts of the formula (III) are generally known, readily available compounds.

Diluents which can be used for the reaction according to the invention are water and all inert organic solvents, especially alcohols, such as methanol and ethanol, ketones, such as acetone, and ethers, such as diethyl ether and dioxane.

The reaction temperatures can be varied within a fairly wide range. In general, the reaction is carried out at between 0° and 40° C, preferably between 15° and 25° C.

In carrying out the process according to the invention, the stoichiometric amount, dependent upon the oxidation level of the metal, of the compound of the formula (II) is employed per mole of the metal salts (III). It is possible to exceed these ratios by up to 20 mol % without significant reduction in yield. Working up is carried out in a generally known manner customary for organic compounds.

The active compounds according to the invention exhibit a powerful fungitoxic action. They do not harm crop plants in the concentrations required to combat fungi. For these reasons, they are suitable for use as plant-protection agents for combating fungi. Fungitoxic agents are employed in plant protection for combating Archimycetes, Phycomycetes, Ascomycetes, Basidiomycetes and Fungi Imperfecti.

The active compounds according to the invention have a very broad spectrum of action and can be used against parasitic fungi which attack above-ground parts of plants, or which attack plants through the soil, and against seed-borne pathogens.

They display a particularly good action against parasitary fungi on above-ground parts of plants, such as species of Plasmopara, for example against the pathogen of grape downy mildew (Plasmopara viticola), against the pathogen of powdery mildew of apple (*Podosphaera leuchotricha*) and of apple scab (*Fusicladium dendriticum*), against *Piricularia oryzae* and *Pellicularia sasakii* on rice, *Puccinia recondita* and *Erysiphe graminis* on cereals, *Hemileia vastatrix* on coffee, *Mycosphaerella musicola* on bananas and species of *Cercospora* on groundnuts.

The compounds according to the invention are well tolerated by plants. They only have a low toxicity to warm-blooded animals and because of their low odor, and their good toleration by human skin, they are not unpleasant to handle.

Many of the compounds also exhibit bactericidal and plant growth-regulatory activity.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as freon; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide etc.), sulfoxides (e.g. dimethyl sulfoxide, etc.), acetonitrile, ketones (e.g. acetone, methyl ethyl ketone methyl isobutyl ketone, cyclohexanone, etc.), and/or water; as well as inert dispersible finely divided solid carriers, such as ground natural minerals (e.g. kaolins, clays, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other fungicides, bactericides and plant growth-regulating compounds, or insecticides, acaricides, rodenticides, herbicides, fertilizers, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0001–10%, preferably 0.01–1%, by weight of the mixture. Thus, the present invention contemplates over-all compositions which comprise mixtures of a conventional dispersible carrier vehicle such as (1) a dispersible inert finely divided carrier solid, and/or (2) a dispersible carrier liquid such as an inert organic solvent and/or water preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

When used as leaf fungicides, the active compound concentrations in the use forms can be varied within a substantial range. They are generally about 0.1 to 0.00001 per cent by weight, preferably about 0.05 to 0.0001%.

Furthermore, the present invention contemplates methods of selectively killing, combating or controlling pests, e.g., fungi and bacteria, and of controlling plant growth, and more particularly methods of combating fungi, which comprises applying to at least one of correspondingly (a) such fungi, (b) such bacteria, (c) such plants, and (d) the corresponding habitat thereof, i.e., the locus to be protected, e.g., to a growing crop, to an area where a crop is to be grown or to a domestic animal, a correspondingly combative, toxic or regulatory amount, i.e., a fungicidally, bactericidally or growth-regulatory effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, dry dressing, moist dressing, wet dressing, encrusting, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limitation, by the following examples:

EXAMPLE 1

Plasmopara Test

Solvent: 4.7 parts by weight of acetone

Dispersant: 0.3 part by weight of alkylaryl polyglycol ether

Water: 95 parts by weight

The amount of active compound required for the desired concentration of active compound in the spray liquid was mixed with the stated amount of solvent, and the concentrate was diluted with the stated amount of water which contained the stated dispersing agent.

Young potted vines (variety Muller-Thurgau) with 2–6 foliage leaves were sprayed with the spray liquid until dripping wet. The plants remained in a greenhouse for 24 hours at 20° C and a relative atmospheric humidity of 70%. The vines were subsequently inoculated with an aqueous spore suspension of *Plasmopara viticola*. The plants were brought into a moist chamber with an atmospheric humidity of 100% and a temperature of 20°–22° C.

After 5 days, the infection of the vines was determined as a percentage of the untreated but also inoculated control plants. 0% means no infection, 100% means that the infection was exactly as great as in the case of the control plants.

The active compounds, the concentrations of the active compounds and the results can be seen from the following Table:

Solvent: 4.7 parts by weight of acetone
Emulsifier: 0.3 part by weight of alkylaryl polyglycol ether
Water: 95 parts by weight The amount of active compound required for the desired concentration of the active compound in the spray liquid was mixed with the stated amount of solvent, and the concentrate was diluted with the stated amount of water which contained the stated emulsifier.

Young apple seedlings in the 4 – 6 leaf stage were sprayed with the spray liquid until dripping wet. The plants remained in a greenhouse for 24 hours at 20° C and at a relative atmospheric humidity of 70%. They were then inoculated by dusting with conidia of the apple powdery mildew causative organism (*Podosphaera leucotricha*) and placed in a greenhouse at a temperature of 21°–23° C and at a relative atmospheric humidity of about 70%.

Ten days after the inoculation, the infection of the seedlings was determined as a percentage of the untreated but also inoculated control plants.

0% means no infection; 100% means that the infection was exactly as great as in the case of the control plants.

Table 3

Plasmopara test

| Active compound | Infection in % of the infection of the untreated control at an active compound concentration of 0.0025% |
|---|---|
| (known) (A) — Cl-phenyl-O-CH-CO-C(CH$_3$)$_3$ with N-imidazole | 72 |
| (known) (B) — dichlorophenyl-O-CH-CO-C(CH$_3$)$_3$ with N-imidazole | 65 |
| (4) [Cu(Cl-C$_6$H$_4$-O-CH(N-imidazole)-CO-C(CH$_3$)$_3$)$_2$]Cl$_2$ | 48 |
| (11) [Cu(Cl$_2$-C$_6$H$_3$-O-CH(N-imidazole)-CO-C(CH$_3$)$_3$)$_2$]Cl$_2$ | 48 |

EXAMPLE 2

Podosphaera test (powdery mildew of apples) [Protective]

The active compounds, the concentrations of the active compounds and the results can be seen from the following Table:

plants remained in a greenhouse for 24 hours at 20° C and at a relative atmospheric humidity of 70%. They were then inoculated with an aqueous conidium sus- Table 4

Podosphaera test/protective

| Active compound | Infection in % of the infection of the untreated control at an active compound concentration of 0.00062% |
|---|---|
| (known) (A) — Cl-phenyl-O-CH(N-triazole)-CO-C(CH₃)₃ | 20 |
| (5) [Cu{Br-phenyl-O-CH(N-triazole)-CH(OH)-C-(CH₃)₃}₄]Cl₂ | 4 |
| (15) [Cu{Cl-phenyl-O-CH(N-triazole)-CH(OH)-C(CH₃)₃}₄]Cl₂ | 0 |
| (6) [Zn{biphenyl-O-CH(N-triazole)-CO-C(CH₃)₃}₂]Cl₂ | 4 |

EXAMPLE 3

Fusicladium test (apple scab) (Protective)
Solvent: 4.7 parts by weight of acetone
Emulsifier: 0.3 part by weight of alkylaryl polyglycol ether
Water: 95 parts by weight The amount of active compound required for the desired concentration of the active compound in the spray liquid was mixed with the stated amount of solvent, and the concentrate was diluted with the stated amount of water which contained the stated emulsifier.

Young apple seedlings in the 4–6 leaf stage were sprayed with the spray liquid until dripping wet. The pension of the apple scab causative organism (*Fusicladium dendriticum*) and incubated for 18 hours in a humidity chamber at 18°–20° C and at a relative atmospheric humidity of 100%.

The plants were then brought into a greenhouse for 14 days.

15 days after inoculation, the infection of the seedlings was determined as a percentage of the untreated but also inoculated control plants.

0% means no infection; 100% means that the infection was exactly as great as in the case of the control plants.

The active compounds, the concentrations of the active compounds and the results can be seen from the following Table:

Table 5

Fusicladium test/protective

| Active compound | Infection in % of the infection of the untreated control at an active compound concentration of | |
|---|---|---|
| | 0.00125% | 0.00062% |
| 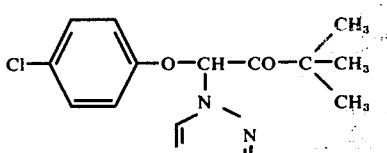 (known) (A) | 14 | 41 |
| 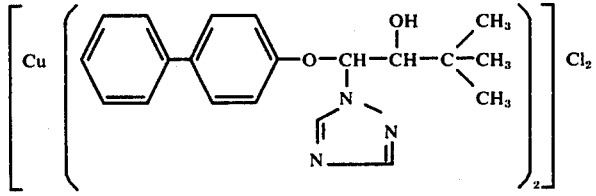 (17) | 0 | 1 |
| 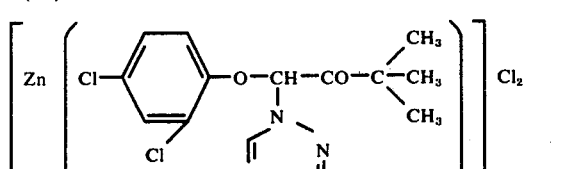 (20) | 4 | 4 |
| 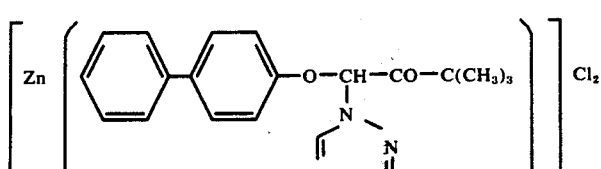 (6) | 0 | 0 |

The process of the present invention is illustrated by the following preparative Examples.

EXAMPLE 4

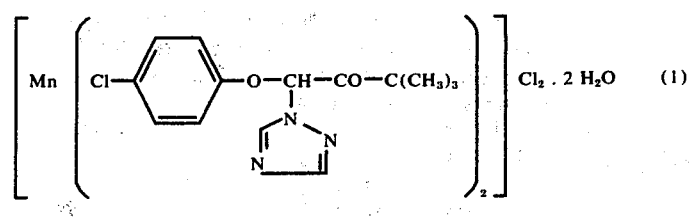

10 g (0.05 mole) of manganese dichloride (MnCl$_2$ . 4 H$_2$O) were dissolved in 50 ml of ethanol and the solution was added dropwise, while stirring, to 29.3 g (0.1 mole) of 1-[1,2,4-triazolyl-(1)]-1-(p-chlorophenoxy)-3,3-dimethyl-butan-2-one, dissolved in 100 ml of ethanol. The solvent was distilled off in a waterpump vacuum. 200 ml of ether were added to the residue and the mixture was stirred for 15 hours at room temperature. The desired product separated out in the form of crystals, which were filtered off. 28.3 g (76% of theory) of bis(1-[1,2,4-triazolyl-(1)]-1-(p-chlorophenoxy)-3,3-dimethyl-butan-2-one)manganese (II) chloride dihydrate of melting point 218°–222° C were obtained.

EXAMPLE 5

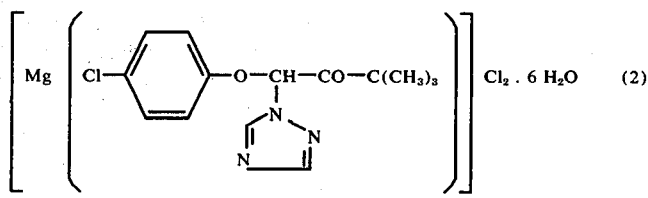

(2)

10.2 g (0.05 mole) of magnesium dichloride (MgCl₂ . 6 H₂O) were dissolved in 50 ml of ethanol and the solution was added dropwise, while stirring, to 14.7 g (0.05 mole) of 1-[1,2,4-triazolyl-(1)]-1-(p-chlorophenoxy)-3,3-dimethyl-butan-2-one, dissolved in 100 ml of ethanol. The solvent was distilled off in a waterpump vacuum and 50 ml of acetone were added to the oily residue. The mixture was stirred for 15 hours at room temperature and the crystalline product which resulted was filtered off. 22.2 g (90% of theory) of mono-[1-(1,2,4-triazolyl-1)-1-(p-chlorophenoxy)-3,3-dimethyl-butan-2-one]magnesium (II) chloride hexahydrate of melting point 128°–132° C were obtained.

EXAMPLE 6

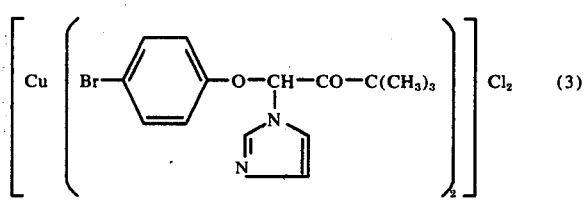

(3)

3.07 g (0.018 mole) of copper dichloride (CuCl₂ . 2 H₂O) were dissolved in 6 ml of H₂O and the solution was added dropwise, while stirring, to 11.1 g (0.033 mole) of 1-(imidazolyl)-1-(p-bromophenoxy)-3,3-dimethyl-butan-2-one, dissolved in 100 ml of ethanol. The turquoise-colored crystals which thereupon precipitated were filtered off and washed with ether. 12 g (99% of theory) of bis-[1-(imidazolyl)-1-(p-bromphenoxy)-3,3-dimethyl-butan-2-one]copper(II) chloride of melting point 107°–109° C were obtained.

EXAMPLE 7

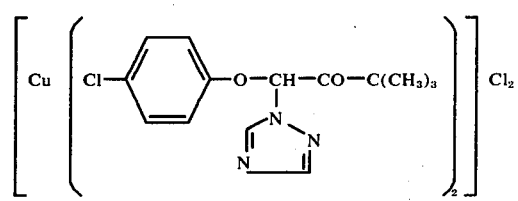

4.4 g (0.025 mole) of copper dichloride (CuCl₂ . 2 H₂O) were dissolved in 6 ml of water and the solution was added dropwise, while stirring, to 14. 7 g (0.05 mole) of 1-[1,2,4-triazolyl-(1)]-1-(p-chlorophenoxy)-3,3-dimethyl-butan-2-one, dissolved in 100 ml of ethanol. After stirring for one hour at room temperature, the turquoise-colored crystals were filtered off. 16 g (89% of theory) of bis-[1-(1,2,4-triazolyl-(1))-1-(p-chlorophenoxy)-3,3-dimethyl-butan-2-one] copper (II) chloride of melting point 103°–104° C were obtained.

EXAMPLE 8

Preparation of the starting compound:

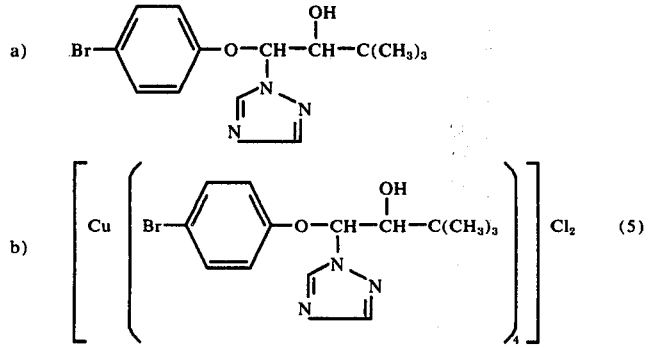

4.4 g (0.025 mole) of copper dichloride (CuCl₂ . 2 H₂O) were dissolved in 20 ml of water and the solution was added dropwise, while stirring, to 17 g (0.05 mole) of 1-[1,2,4-triazolyl-(1)]-1-(p-bromophenoxy)-3,3-dimethyl-butan-2-ol, dissolved in 300 ml of ethanol.

The solution was concentrated to half its volume and 100 ml of water were added. A green oil separated out. The aqueous phase was decanted off and the organic phase was stirred for 30 minutes with 80 ml of diisopropyl ether. The resultant green crystals were then filtered off. 5.5 g (54% of theory) of tetra-[1-(1,2,4-triazolyl-(1))-1-(p-bromophenoxy)-3,3-dimethyl-butan-2-ol] copper(II) chloride of melting point 92°–95° C were obtained.

676 g (2 moles) of 1-[1,2,4-triazolyl-(1)]-1-(p-bromophenoxy)-3,3-dimethyl-butan-2-one were dissolved in 3 l of methanol. A total of 80 g (2 moles) of sodium borohydride was added thereto, in portions of 5 g, at 0° to 10° C while stirring and cooling with ice, and the mixture was stirred for 2 hours at 5° to 10° C and then for 12 hours at room temperature. It was then cooled to 10° C and 300 g (3 moles) of concentrated aqueous hydrochloric acid were added at 10° to 20° C. After stirring for six hours at room temperature, the resulting suspension was diluted with 3.8 l of water which contained 400 g (4.8 moles) of sodium bicarbonate. The precipitate thereby produced was filtered off. 546.5 g (85% of theory) of 1-[1,2,4-triazolyl-(1)]-1-(p-bromophenoxy)-3,3-dimethyl-butan-2-ol of melting point 115°–118° C were obtained.

EXAMPLE 9

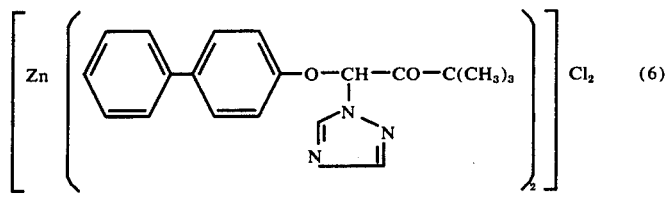

3.4 g (0.025 mole) of ZnCl₂ were dissolved in 20 ml of ethanol and the solution was added dropwise, while stirring, to 16.8 g (0.05 mole) of 1-[1,2,4-triazolyl-(1)]-1-(p-phenylphenoxy)-3,3-dimethyl-butan-2-one, dissolved in 300 ml of ethanol. After stirring for 30 minutes at room temperature, the resulting precipitate was filtered off and rinsed with a little ethanol. 15 g (74% of theory) of bis-[1-(1,2,4-triazolyl-(1))-1-(p-phenylphenoxy)-3,3-dimethyl-butan-2-one]zinc(II) chloride of melting point 182° C were obtained.

EXAMPLE 10

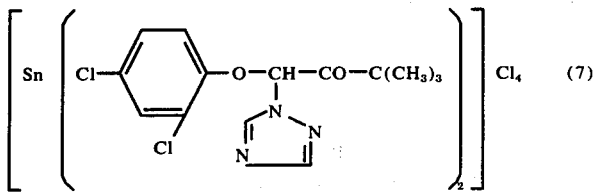

10.4 g (0.04 mole) of tin tetrachloride (SnCl₄) were added dropwise, while stirring, to 24.6 g (0.075 mole) of 1-[1,2,4-triazolyl-(1)]-1-(2,4-dichlorophenoxy)-3,3-dimethyl-butan-2-one, dissolved in 200 ml of ethanol. The solvent was then distilled off in a waterpump vacuum. 50 ml of n-pentane were added to the residue and the mixture was left to stand for 4 days at 0° C. The colorless crystals which had separated out after this time were filtered off and rinsed with 20 ml of diisopropyl ether. 29.9 g (87% of theory) of bis-[1-(1,2,4-triazolyl-(1))-1-(2,4-dichlorophenoxy)-3,3-dimethyl-butan-2-one]tin(IV) chloride of melting point 216°–218° C were obtained.

EXAMPLE 11 a. [2-(2,4-dichlorophenoxy)-4,4-dimethyl-pentan-3-onyl]-diethylmethylammonium iodide of the formula

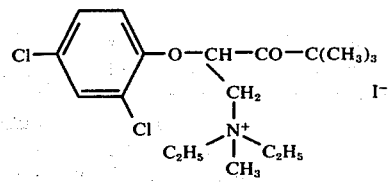

required for the preparation of the above intermediate was prepared as follows:

234.2 g (0.9 mole) of 2-(2,4-dichlorophenoxy)-4,4-dimethyl-pentan-3-one, 110 g (1 mole) of diethylammonium chloride and 45 g (1.5 moles) of paraformaldehyde were dissolved in 300 ml of anhydrous ethanol. 2 ml of concentrated hydrochloric acid were added and the reaction mixture was heated to the boil under reflux for 2 hours. After addition of a further 30 g (1 mole) of paraformaldehyde, the mixture was again heated for 2 hours under reflux and was then left to stand overnight at room temperature. The batch was poured into 1.2 l of water and extracted with 1.5 l of ether. The aqueous phase was adjusted to pH 8 with ammonia solution and again extracted with 1 l of ether. The combined ether phases were dried over sodium sulfate and freed from the solvent in vacuo. The resulting yellow oil — 177 g (52.2% of theory) of [2-(2,4-dichlorophenoxy)-4,4-dimethyl-pentan-3-onyl]-diethylammonium chloride — did not crystallize and was therefore reacted further in the form of the crude product.

38.1 g (0.1 mole) of [2-(2,4-dichlorophenoxy)-4,4-dimethyl-pentan-3-onyl]-diethylammonium chloride were dissolved in 200 ml of anhydrous tetrahydrofuran and 20.2 g (0.2 mole) of triethylamine were added dropwise at room temperature. After stirring for quarter of an hour at room temperature, the triethylammonium chloride which had precipitated was filtered off and the solvent was distilled off in vacuo. 30.9 g (90% of theory) of [2-(2,4-dichlorophenoxy)-4,4-dimethyl-pentan-3-onyl]-diethylamine were obtained as a yellow oil, which was immediately dissolved in 300 ml of anhydrous acetonitrile (0.09 molar batch). 21.3 g (0.15 mole) of methyl iodide were added dropwise thereto at room temperature, while stirring. The reaction mixture was stirred for 1 hour at room temperature and for 30 minutes under reflux and thereafter the solvent was distilled off under reduced pressure. The oil residue was taken up in 200 ml of a mixture of ethyl acetate and methyl ethyl ketone (1:1) and the whole was heated to the boil. This produced a crystalline residue, which was filtered off and rinsed with ether. 22.8 g (51.6% of theory) of [2-(2,4-dichlorophenoxy)-4,4-dimethyl-pentan-3-onyl]-diethylmethylammonium iodide of melting point 114°–118° C were obtained.

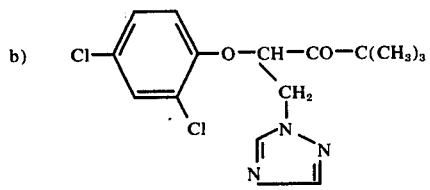

22.6 g (0.0464 mole) of [2-(2,4-dichlorophenoxy)-4,4-dimethyl-pentan-3-onyl]-diethylmethylammonium iodide were dissolved in 250 ml of anhydrous acetonitrile and 10.4 g (0.15 mol) of 1,2,4-triazole were added in portions. After heating for 24 hours under reflux, the solvent was distilled off under reduced pressure. The oily residue was taken up in 500 ml of methylene chloride and was extracted with twice 600 ml of water. The organic phase was separated off, dried over sodium sulfate and freed from the solvent in vacuo. The oil residue was triturated with diisopropyl ether and thereafter solidified. It was filtered off, well washed with diisopropyl ether and dried. 10.3 g (64.2% of theory) of 1-[1,2,4-triazolyl-(1)]-2-(2,4-dichlorophenoxy)-4,4-dimethyl-pentan-3-one of melting point 75°–77° C were obtained.

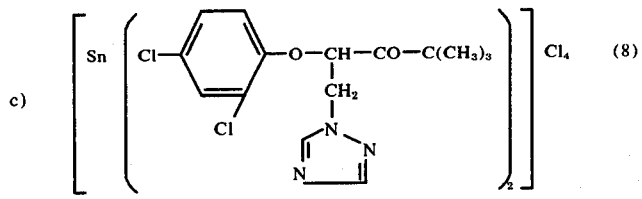

6.5 g (0.025 mole) of tin tetrachloride (SnCl₄) were added dropwise, while stirring, to 17.1 g (0.05 mole) of 1-[1,2,4-triazolyl-(1)]-2-(2,4-dichlorophenoxy)-4,4-dimethyl-pentan-3-one, dissolved in 100 ml of ethanol. The mixture was stirred for a further 2 hours at room temperature. The colorless crystals which had precipitated were filtered off and rinsed with 20 ml of diisopropyl ether. 23 g (97% of theory) of bis-[1-(1,2,4-triazolyl-(1))-2-(2,4-dichlorophenoxy)-4,4-dimethyl-pentan-3-one] tin(IV) chloride of melting point 235°–236° C were obtained.

The following compounds of the general formula

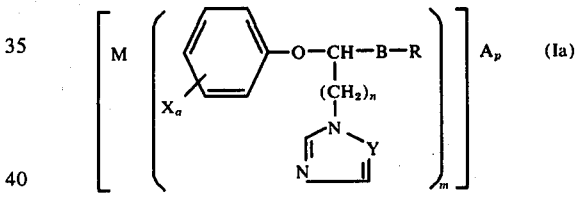

were prepared by methods analogous to those described in Examples 4 to 11.

Table 6

| Compound No. | M | X | a | n | Y | B | R | m | A | P | Melting point (° C) |
|---|---|---|---|---|---|---|---|---|---|---|---|
| 9 | Cu | 4-F | 1 | 0 | N | CO | C(CH₃)₃ | 2 | Cl | 2 | 179 |
| 10 | Cu | 4-NO₂ | 1 | 0 | N | CO | C(CH₃)₃ | 2 | Cl | 2 | 185 |
| 11 | Cu | 2,4-Cl | 2 | 0 | N | CO | C(CH₃)₃ | 2 | Cl | 2 | 142 – 143 |
| 12 | Cu | 4-Br | 1 | 0 | N | CO | C(CH₃)₃ | 2 | Cl | 2 | 109 – 111 |
| 13 | Cu | 4—⌬ | 1 | 0 | N | CO | C(CH₃)₃ | 2 | Cl | 2 | 117 – 120 |
| 14 | Cu | 4-F | 1 | 0 | N | CHOH | C(CH₃)₃ | 2 | Cl | 2 | 167 – 169 |
| 15 | Cu | 4-Cl | 1 | 0 | N | CHOH | C(CH₃)₃ | 4 | Cl | 2 | 136 |
| 16 | Cu | 4-NO₂ | 1 | 0 | N | CHOH | C(CH₃)₃ | 4 | Cl | 2 | 183 – 185 |
| 17 | Cu | 4—⌬ | 1 | 0 | N | CHOH | C(CH₃)₃ | 2 | Cl | 2 | 105 – 107 |
| 18 | Zn | 4-Br | 1 | 0 | N | CO | C(CH₃)₃ | 2 | Cl | 2 | 206 – 209 |
| 19 | Zn | 4-Cl | 1 | 0 | N | CO | C(CH₃)₃ | 2 | Cl | 2 | 192 |
| 20 | Zn | 2,4-Cl | 2 | 0 | N | CO | C(CH₃)₃ | 2 | Cl | 2 | 125 – 128 |
| 21 | Zn | 4-F | 1 | 1 | N | CO | C(CH₃)₃ | 2 | Cl | 2 | 130 – 132 |
| 22 | Zn | — | 0 | 0 | N | CO | C(CH₃)₃ | 2 | Cl | 2 | 141 – 143 |
| 23 | Sn | — | 0 | 0 | N | CO | C(CH₃)₃ | 2 | Cl | 4 | 184 – 187 |
| 24 | Sn | 4-Cl | 1 | 0 | N | CO | C(CH₃)₃ | 2 | Cl | 4 | 173 |
| 25 | Sn | 4—⌬ | 1 | 0 | N | CO | C(CH₃)₃ | 2 | Cl | 4 | 149 – 152 |
| 26 | Cu | 4-Cl | 1 | 0 | N | CO | ⌬ | 2 | Cl | 2 | 146 – 149 |

Table 6-continued

| Compound No. | M | X | a | n | Y | B | R | m | A | P | Melting point (°C) |
|---|---|---|---|---|---|---|---|---|---|---|---|
| 27 | Zn | 4-Cl | 1 | 0 | N | CO | —⟨phenyl⟩ | 2 | Cl | 2 | 205 |
| 28 | Cu | 4-Cl | 1 | 0 | N | CHOH | —⟨phenyl⟩ | 3 | Cl | 2 | 112 – 115 |
| 29 | Cu | 2,4-Cl | 2 | 0 | CH | CO | C(CH₃)₃ | 2 | Cl | 2 | 190 – 193 Z |
| 30 | Sn | 2,4-Cl | 2 | 0 | CH | CO | C(CH₃)₃ | 2 | Cl | 4 | 90 – 110 Z |
| 31 | Zn | 2,4-Cl | 2 | 0 | CH | CO | C(CH₃)₃ | 2 | Cl | 2 | 90 – 106 Z |

It will be appreciated that the instant specification and examples are set forth by way of illustration and not limitation, and that various modifications and changes may be made without departing from the spirit and scope of the present invention.

What we claim is:

1. A metal complex of an azolyl ether of the formula

in which
M is copper, zinc, manganese, magnesium, tin iron or nickel,
X is halogen, nitro, nitrile, amino, alkyl or cycloalkyl with in either case up to 6 carbon atoms, halogenoalkyl with 1 or 2 carbon atoms and up to 5 halogen atoms, hydroxymethyl, phenyl, halogenophenyl, phenyl-substituted phenyl, carboxyl, alkoxycarbonyl or alkylcarbonyloxy with in either case a total of up to 5 carbon atoms, alkoxy or alkylthio with in either case 1 or 2 carbon atoms, halogenoalkoxy or halogenoalkylthio with in either case 1 or 2 carbon atoms and up to 5 halogen atoms, phenoxy, benzoyloxy, chlorophenoxy, chlorobenzoyloxy, benzoyl, chlorobenzoyl, dialkylamino with a total of up to 6 carbon atoms, alkylcarbonyl amino with a total of up to 4 carbon atoms, alkylsulfonyl or alkylsulfonyloxy with in either case 1 or 2 carbon atoms, phenylsulfonyl and phenylsulfonyloxy,
Az is an imidazolyl radical, a 1,2,4-triazolyl-(1) radical or a 1,2,4-triazolyl-(4) radical,
B is CO or CH(OH),
R is alkyl with up to 6 carbon atoms or optionally phenyl substituted in o- or p-position with halogen, nitro, nitrile or methyl,
A is a chloride, bromide, iodide, nitrate, sulfate or phosphate anion,
a is 0 or an integer from 1 to 4,
n is 0 or 1,
m is an integer from 1 to 4,
p is an integer from 1 to 4, and
k is an integer from 0 to 8.

2. The compound according to claim 1 wherein such compound is mono[1-(1,2,4-triazolyl-(1))-1-(p-chlorophenoxy)-3,3-dimethylbutan-2-one]magnesium (II) chloride hexahydrate of the formula

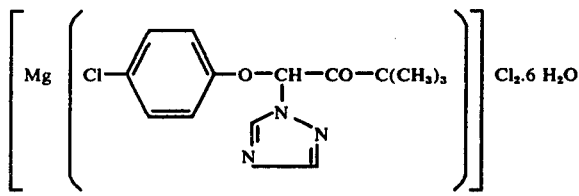

3. The compound according to claim 1, wherein said compound is bis-[1-(1,2,4-triazolyl-(1))-1-(p-chlorophenoxy)-3,3-dimethyl-butan-2-one] copper (II) chloride of the formula

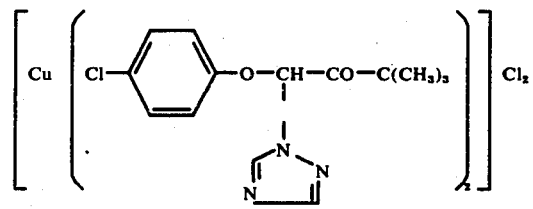

4. The compound according to claim 1, wherein said compound is tetra-[1-(1,2,4-triazolyl-(1))-1-(p-bromophenoxy)-3,3-dimethyl-butan-2-ol] copper(II) chloride of the formula

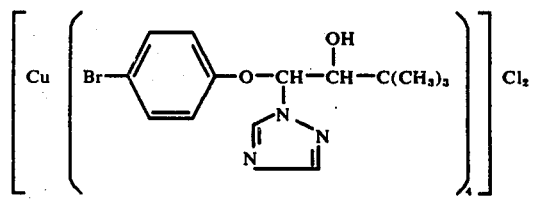

5. The compound according to claim 1, wherein said compound is bis-[1-1,2,4-triazolyl-(1)-1-(p-phenylphenoxy)-3,3-dimethyl-butan-2-one]zinc(II) chloride of the formula

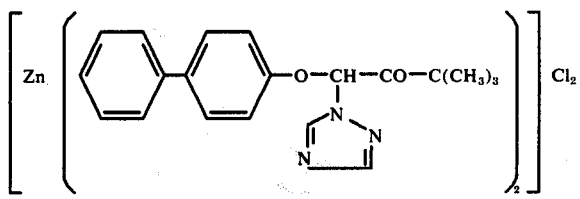

6. The compound according to claim 1, wherein said compound is bis-[1-1,2,4-triazolyl-(1)-1-(2,4-dichlorophenoxy)-3,3-dimethyl-butan-2-one]copper(II)chloride of the formula

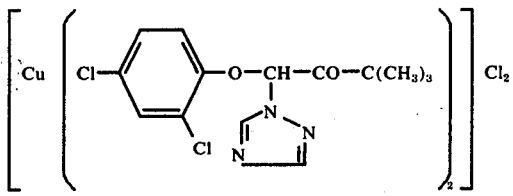

7. The compound according to claim 1, wherein said compound is tetra-[1-1,2,4-triazolyl-(1)-1-(p-chlorophenoxy)-3,3-dimethyl-butan-2-ol]copper(II) chloride of the formula

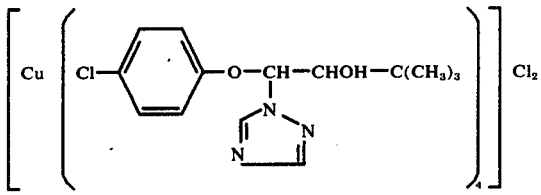

8. The compound according to claim 1, wherein said compound is bis-[1-1,2,4-triazolyl-(1)-1-(p-diphenoxy)-3,3-dimethyl-butan-2-ol]copper(II)chloride of the formula

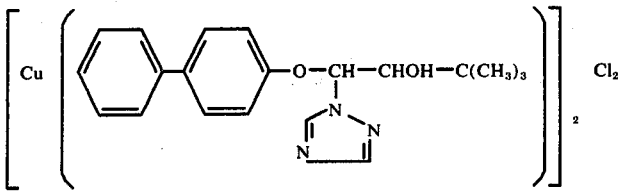

9. The compound according to claim 1, wherein said compound is bis-[1-1,2,4-triazolyl-(1)-1-(2,4-dichlorophenoxy-3,3-dimethyl-butan-2-ol]zinc(II) chloride of the formula

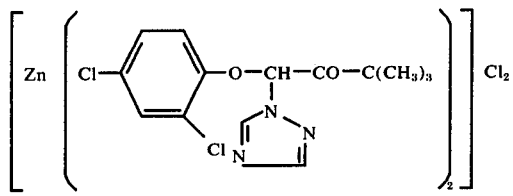

10. A fungicidal composition containing as active ingredient a fungicidally effective amount of a compound according to claim 1 admixture with a diluent.

11. A method of combating fungi which comprises applying to the fungi or a fungus habitat a fungicidally effective amount of a compound according to claim 1.

12. The method according to claim 11 in which said compound is mono[1-(1,2,4-triazolyl-(1)-1-(p-chlorophenoxy)-3,3-dimethylbutan-2-one]magnesium (II) chloride hexahydrate; bis-[1-(1,2,4-triazolyl-(1)-1-(p-chlorophenoxy)-3,3-dimethyl-butan-2-one] copper (II) chloride; tetra-[1-(1,2,4-triazolyl-(1)-1-(p-bromophenoxy)-3,3-dimethyl-butan-2-ol] copper (II) chloride; bis-[1-1,2,4-triazolyl(1)-1-(p-phenylphenoxy)-3,3-dimethyl-butan-2-one]zinc (II) chloride; bis-[1-1,2,4-triazolyl-(1)-1-(2,4-dichlorophenoxy)-3,3-dimethyl-butan-2-one]copper (II) chloride; tetra-[1-1,2,4-triazolyl-(1)-1-(p-chlorophenoxy)-3,3-dimethyl-butan-2-one]copper (II) chloride; bis-[1-1,2,4-triazolyl-(1)-1-(p-diphenoxy)-3,3-dimethyl-butan-2-ol]copper (II) chloride; or bis-[1-1,2,4-triazolyl-(1)-1(2,4-dichlorophenoxy-3,3-dimethyl-butan-2-one]zinc (II) chloride.

* * * * *